(12) United States Patent
Kondo et al.

(10) Patent No.: US 6,248,545 B1
(45) Date of Patent: Jun. 19, 2001

(54) ASSAY OF DENATURED LIPOPROTEINS

(75) Inventors: Akira Kondo; Naoko Toda; Noriko Kobayashi; Masayuki Nozawa; Mitsuhisa Manabe, all of Tokyo (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 08/949,911

(22) Filed: Oct. 14, 1997

Related U.S. Application Data

(63) Continuation of application No. 08/327,105, filed on Oct. 21, 1994, now abandoned.

(30) Foreign Application Priority Data

Oct. 22, 1993 (JP) ...................................... 5-264809
Aug. 2, 1994 (JP) ...................................... 6-181329
Aug. 12, 1994 (JP) ...................................... 6-190279

(51) Int. Cl.$^7$ ............................ G01N 33/53; G01N 33/92
(52) U.S. Cl. ...................... 435/7.94; 435/7.95; 435/7.1; 436/518; 436/71; 436/176
(58) Field of Search ..................... 435/7.1, 7.9, 7.92, 435/7.94, 7.95; 436/518, 524, 528, 63, 71, 173, 176

(56) References Cited

U.S. PATENT DOCUMENTS 4,376,110 * 3/1983 David et al. .
5,270,165 * 12/1993 Von Nostrand et al. .
5,766,590 * 6/1998 Founds et al. .

FOREIGN PATENT DOCUMENTS 0 361 468 A1  4/1990 (EP) .
0484863 * 5/1992 (EP) .

OTHER PUBLICATIONS

Nakamura et al, Handbook of Experimental Immunology, 1986 Blackwell Scientific Publications, pp. 27.1–27.20.*
Dubois et al., Journal of Immunological Methods, 125:215–223, 1989.*
Marcel et al. J. Biol. Chem, vol. 259 No. 11, 1984, 6952–6957.*
Campbell et al in Laboratory Techniques in Biochemistry & Molecular Biology vol. 23, p. 2, published 1991. by Elsevier Science, NY, NY.*
Mazière et al., *Atherosclerosis,* 104, 1993, 213–219.
Morel, *Biochemical and Biophysical Research Communications,* vol. 200, No. 1, Apr. 15, 1994, 408–416.
Salmon et al., *Biochimica et Biophysica Acta,* 920, 1987, 215–220.
Gonen et al., *Artherosclerosis,* 65, 1987, 265–272.
Fogelman et al., *Proc. Natl. Acad. Sci. USA,* 77, No. 4, Apr. 1980, 2214–2218.
Quinn et al., *Proc. Natl. Acad. Sci. USA,* 84, May 1987, 2995–2998.
Loscalzo, *Arteriosclerosis,* 10, No. 5, Sep./Oct. 1990, 672–678.
Haberland et al., *The Journal of Biological Chemistry,* 267, No. 6, Feb. 25, 1992, 4143–4151.
*Arteriosclerosis,* 10, No. 5, Sep./Oct. 1990, p. 812a.
Fless et al., *Journal of Lipid Research,* 30, 1989, 651662.
No Author "Pharmacology", *Chemical Abstracts,* vol. 116, No. 7, Feb. 17, 1992.

* cited by examiner

*Primary Examiner*—Patricia A. Duffy
(74) *Attorney, Agent, or Firm*—Bacon & Thomas

(57) ABSTRACT

Disclosed herein is an assay of a denatured lipoprotein, in which the denatured site of the denatured lipoprotein contained in a vital sample is exposed to the surface of its lipoprotein particle upon the reaction of an antibody, which recognizes the denatured lipoprotein, with the vital sample containing the denatured lipoprotein.

26 Claims, 11 Drawing Sheets

□ : ——————  SDS
+ : 0.75 mM  SDS
● : 2.25 mM  SDS
△ : 3.75 mM  SDS
× : 5.25 mM  SDS

○ : MDA-LDL
□ : LDL
● : VLDL + IDL
■ : HDL

☐ : ——— Sodium dodecylbenzenesulfonate

＋ : 8.6mM Sodium dodecylbenzenesulfonate

Effect of SDS on assaying system

○ : SDS   0   mM
□ : SDS   3.75 mM
● : SDS   6.75 mM
■ : SDS   9.75 mM
△ : SDS  15.75 mM

Assay of MDA-Lp(a): Inhibition by MDA-HSA

O : HSA

□ : MDA-HSA

Effect of sodium dodecylbenzenesulfonate on assaying system

○ : Sodium dodecylbenzenesulfonate    0 mM
□ :    ″    1 mM
● :    ″    5 mM
■ :    ″    10 mM Effect of cetyltrimethylammonium chloride on assaying system

| | | | |
|---|---|---|---|
| ○ : | Cetyltrimethylammonium chloride | | 0 mM |
| □ : | 〃 | | 5 mM |
| ● : | 〃 | | 10 mM |
| ■ : | 〃 | | 20 mM |

Effect of polyoxyethylene secondary alkyl ether on assaying system

○ : Polyoxyethylene secondary alkyl ether   0 %
□ :                  〃                    0.05%
● :                  〃                    0.2%
■ :                  〃                    0.5%

ASSAY OF DENATURED LIPOPROTEINS

This application is a Continuation of application Ser. No. 08/327,105, filed Oct. 21, 1994, now abandoned.

BACKGROUND OF THE INVENTION

1. Field of the Invention

The present invention relates to a reliable assay of denatured lipoproteins which are considered to involve arteriosclerosis and present in the living body.

2. Description of the Background Art

Arteriosclerosis is known to be the main cause of ischemic heart diseases, cerebral infarction and the like. The mechanism causative of arteriosclerosis is reported to form atheroma due to accumulation of smooth muscle cells, connective tissues and a great amount of lipids (mainly, cholesterol esters) on a vascular subendothelium, resulting in the hypertrophy of the arterial wall and advanced induration, which finally brings about the hypofunction of the artery. In particular, it is considered that the atheroma recognized in the initial lesion of this disease is formed from foam cells produced by the accumulation of a denatured low density lipoprotein (LDL) into macrophages. However, the true character of the denatured LDL which transforms the macrophages into the foam cells in the living body is unknown to date. However, it has recently been explicated that there is a possibility that two kinds of denatured LDLS one of which is a denatured LDL formed by the interaction between a vascular endothelial cell which is reported to play an important role in arteriosclerosis and LDL [Quinn, M. T., Parthasarathy, S., Fong, L. G. & Steingerg, D., Proc. Natl. Acad. Sci. USA, 84, 2995–2998 (1987)], and the other of which is an LDL modified with malondialdehyde (MDA) known as an end metabolic product of lipid peroxides and thromboxane $A_2$, which also play an important role in arteriosclerosis [Fogelman, A. M., Shechter, I., Seager, J., Hokom, M., Child, J. S. & Bdwards, P. A., Proc. Natl. Acad. Sci. USA, 77, 2214–2218 (1980)], may deeply participate in the initial lesion of arteriosclerosis. An assay of these denatured LDLs in the living body has hence been regarded as important.

Some methods have heretofore been reported as methods for assaying denatured LDLs. For example, Gonen et al., and Salmon et al. apply an EIA competition analysis in which MDA-modified LDL coated on the plate, and an antibody which recognizes the MDA-modified LDL are used [Gonen, B., Fallon, J. J. & Baker, S. A, Atherosclerosis, 65, 265–272 (1987)] and an EIA sandwich technique in which an immobilized antibody which recognizes MDA-modified LDL and an enzyme-labeled antibody which recognizes LDL are used [Salmon, S., Maziere, C., Theron, L., Beucler, I., Ayrault-Jarrier, M., Goldstein, S. & Polonovski, J., Biochim. Biophys. Acta, 920, 215–22 (1987)], respectively, to assay extracts from a focus of arteriosclerosis or the MDA-modified LDL in the blood However, Gonen et al. have failed to detect the MDA-modified LDL in the arteriosclerosis tissue according to this analysis. On the other hand, Salmon et al. have reported that although the assay of the MDA-modified LDL in the blood was performed as to 65 specimens, only 14 specimens were able to be detected, but the residual 51 specimens were unable to be detected.

As described above, it has heretofore been known to assay MDA-modified LDL artificially synthesized. It has however been impossible to effectively assay MDA-modified LDL, i.e., a denatured LDL, in vital samples.

On the other hand, it has been known that lipoprotein (a) [Lp(a)] involves the causation of the coronary artery disease independent of other risk factors in the causation of arteriosclerotic diseases. In recent years, attention has been paid to the participation of a denatured Lp(a) as a mechanism causative of this disease [Loscalzo. J., Arteriosclerosis, 10, 672–679 (1990)], that is to say, a mechanism that the denatured Lp(a) accumulates on the coronary artery, and macrophages attracted thereto incorporate it therein, whereby they are transformed into foam cells. As recent reports supporting this hypothesis, may be mentioned a report that when Lp(a) is treated with copper or modified with malondialdehyde (MDA) to be converted to a denatured Lp(a) having a minus charge, its engorgement into macrophages increases [Haberland, M. E., Fless, G. M., Scanu, A. M. & Fogelman, A. M., J. Biol. Chem., 267, 4143–4151 (1992)], and a report that Lp(a) accumulates on a focus of arteriosclerosis, and this Lp(a) has a more negative charge compared with native (normal) Lp(a) as determined by agarose electrophoresis [O'Neil, J. A., Pepin, J. M., Smejkal, G., et al, Arteriosclerosis, 10, 812a (1990)].

As described above, it has been explicated that denatured Lp(a)s have a possibility of deeply participating in the causation of arteriosclerosis, and an assay of the denatured Lp(a)s in the living body has hence been regarded as important.

A great number of methods have heretofore been reported as methods for assaying denatured Lp(a)s in the living body. For example, Fless et al. have established an EIA sandwich technique making good use of a likeness of Lp(a) to a product obtained by binding LDL with apo(a), in which an antibody which recognizes apoB, i.e., a main structural protein, and another antibody which recognizes apo(a) are used [Fless, G. M., Snyder, M. L. & Scanu, A. M., Lipid Res., 30, 651–662 (1989)].

As described above, it has heretofore been known to assay Lp(a). However, these methods are not intended to specifically detect denatured Lp(a)s in vital samples, which are considered to have a possibility of more deeply participating in the causation of arteriosclerosis.

On the other hand, among various kinds of lipoproteins, those in which the existence of denatured lipoproteins has been recognized include high density lipoprotein (HDL) and the like. However, no assay has been yet developed even on these denatured lipoproteins [Morel, D. W., Biochem. Biophys. Res. Commun., 200, 408–416 (1994); Maziere, J. C., Myara, I., Santus, R. & Mazier E. C., Atherosclerosis, 104, 213–219 (1993)].

SUMMARY OF THE INVENTION

Therefore, it is an object of the present invention to provide a method of selectively assaying denatured lipoproteins in vital samples.

In view of the foregoing circumstances, the present inventor has carried out an extensive investigation. As a result, it has been found that the fact that even when an antibody (hereinafter referred to as "anti-denatured lipoprotein antibody") which recognizes a denatured lipoprotein is used, the denatured lipoprotein in the living body can not be assayed is attributed to the fact that the denatured site of the denatured lipoprotein is hidden in the interior of its lipoprotein particle, whereby the denatured lipoprotein is inactivated, and hence that if this denatured site is exposed to the surface of the lipoprotein particle, the denatured lipoprotein can react with the anti-denatured lipoprotein antibody to selectively assay it, thus leading to completion of the present invention.

In an aspect of the present invention, there is thus provided an assay of a denatured lipoprotein, which comprises exposing the denatured site of the denatured lipoprotein contained in a vital sample to the surface of its lipoprotein particle upon the reaction of an anti-denatured lipoprotein antibody with the vital sample containing the denatured lipoprotein.

According to the present invention, the denatured site of a denatured lipoprotein, which has been hidden in the interior of its lipoprotein particle, can be exposed to the surface of the lipoprotein particle to succeed in reaction with the anti-denatured lipoprotein antibody, whereby the denatured lipoprotein in the living body can be reliably assayed.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
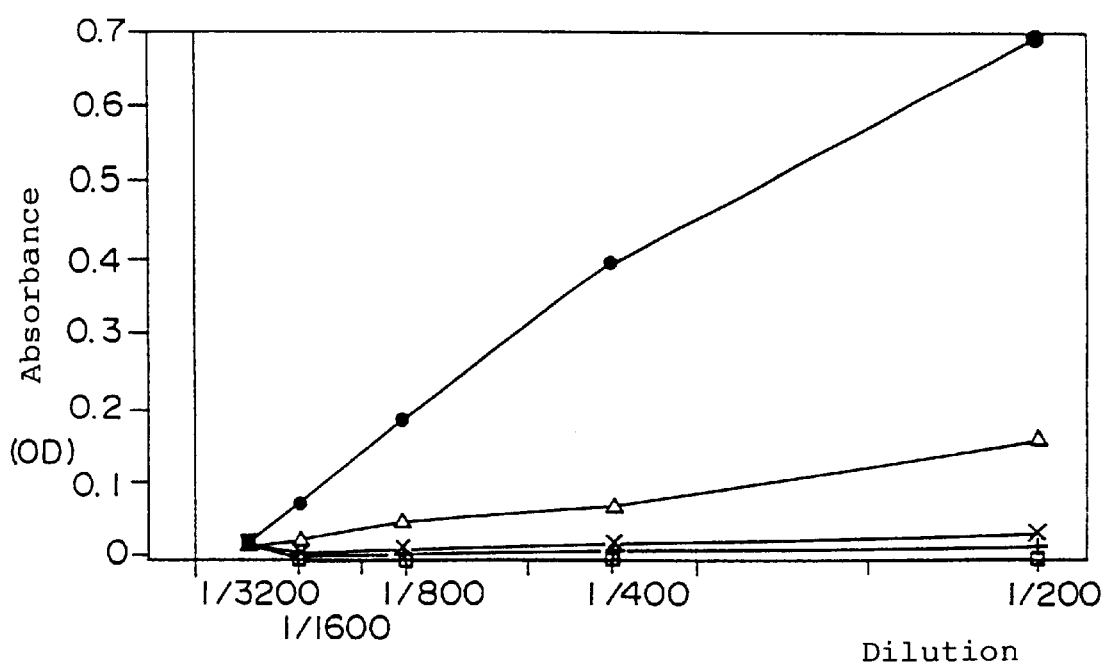
FIG. 1 diagrammatically illustrates the effect of sodium dodecyl sulfate (SDS) on an assaying system for MDA-modifed LDL in a human serum using an anti-human MDA-modified LDL monoclonal antibody.

Denatured lipoproteins intended to be assayed in the present invention include denatured LDL, denatured Lp(a), denatured HDL and the like. As described above, the denatured LDL deeply participates in the causation of arteriosclerosis. Besides, the denatured Lp(a) deeply participates in the causation of sclerosis particularly in a coronary artery among arteries. Further, the denatured HDL also deeply participates in the causation of arteriosclerosis.

No particular limitation is imposed on the vital sample used in the present invention so far as it is a sample in which a denatured lipoprotein may exist. However, samples thereof include blood, plasma, serum and the like. Of these, plasma or serum is particularly preferred.

The anti-denatured lipoprotein antibody used in the present invention may be either a polyclonal antibody or a monoclonal antibody so far as it reacts with the denatured lipoprotein, but does not react with its normal lipoprotein. However, the monoclonal antibody is preferred. Examples of the anti-denatured lipoprotein antibody include anti-MDA-modified lipoprotein antibodies and anti-hapten antibodies which recognize an MDA residue. Of these, anti-MDA-modified lipoprotein monoclonal antibodies are particularly preferred. Specific examples thereof include an anti-MDA-modified LDL antibody, an anti-MDA-modified Lp(a) antibody and an anti-MDA-modified HDL antibody. In the case of Lp(a), the anti-MDA-modified LDL antibody may be used because it has almost similar composition of LDL binding with apo(a). The monoclonal antibody can be produced in the following manner in accordance with, for example, the method described in Japanese patent Application Laid-Open No. 173096/1992.

A purified lipoprotein is first prepared from a fresh human serum by an ultracentrifugation known per se in the art. MDA is then reacted with this lipoprotein to prepare an MDA-modified lipoprotein. The MDA-binding reaction of the lipoprotein is preferably performed for 30 minutes to 24 hours usually at a pH of 6–7 and a reaction temperature of 20–40° C. Since this reaction can be stopped by cooling the reaction mixture to 4° C., the reaction mixture is cooled to 4° C. to stop the reaction. The reaction mixture thus cooled is dialyzed at 4° C. to a buffer solution kept at pH 6–8 and added with 10–100 $\mu$M of EDTA as needed.

This human MDA-modified lipoprotein can be used as an immunogen to prepare an anti-human MDA-modified lipoprotein monoclonal antibody by an already-known cell fusion means. More specifically, a mouse is immunized to the human MDA-modified lipoprotein, and a spleen is taken out of the mouse after a predetermined period of time. After the cell of the spleen taken out is fused with a myeloma cell in the presence of polyethylene glycol, the fused cell is cultured for a predetermined period of time, whereby a hybridoma strain which produces an anti-human MDA-modified lipoprotein monoclonal antibody high in specificity can be obtained owing to a difference in reactivity to the lipoprotein and the MDA-modified lipoprotein among antibodies produced in a culture supernatant.

The thus-obtained hybridoma cell strain is cultured in vitro or in vivo to obtain an anti-MDA-modified lipoprotein antibody.

As a means for exposing the denatured site of the denatured lipoprotein in a vital sample to the surface of its lipoprotein particle, which is most important in the present invention, may be mentioned a surfactant treatment.

More specifically, when a surfactant is caused to act on the denatured lipoprotein in the living body, the lipoprotein undergoes a structural change, whereby the denatured site hidden in the interior of the lipoprotein particle is exposed to the surface of the lipoprotein particle. In the method of the present invention, the surfactant is caused to coexist in a reaction system containing the vital sample and the anti-denatured lipoprotein antibody. As a result, a reaction of the antibody with the denatured lipoprotein takes place, whereby the denatured lipoprotein in the vital sample can be selectively assayed.

Examples of the surfactant used include anionic surfactants, cationic surfactants, amphoteric surfactants and nonionic surfactants. Of these, the anionic surfactants are preferred. For example, mono- or di-$C_{8-18}$ alkyl quaternary ammonium salts, $C_{8-18}$ alkylsulfates, $C_{8-18}$ alkylbenzenesulfonates, $C_{8-18}$ alkylphosphates, $C_{8-18}$ alkyl ether sulfates, $C_{8-18}$ alkyl ether benzenesulfonates, polyoxyethylene secondary alkyl ethers and the like may be mentioned. Of these, cetyltrimethylammonium chloride, benzalkonium chloride, sodium dodecyl sulfate (SDS), sodium dodecylbenzenesulfonate, diethanolamine alkylphosphates, polyoxyethylene secondary alkyl ethers (added with 9 mols of ethylene oxide) are particularly preferred. The surfactant may preferably be used in a concentration ranging from 0.1 to 50 mM, particularly from 0.5 to 20 mM. In particular, SDS may preferably be used in a range of 1–5 mM.

No particular limitation is imposed on the means for assaying the denatured lipoprotein the denatured site of which has been exposed to the surface of its lipoprotein particle so far as it is an immunoassay known per se in the art. Examples of methods usable in the present invention include immunoturbidimetry, nephelometric immunoassay, latex agglutination method, radioimmunoassay, enzyme immunoassay. In particular, enzyme immunoassay is preferred because it is excellent in specificity, sensitivity and utility.

The method of the present invention will hereinafter be described in detail taking the case of the enzyme immunoassay.

It has been suggested that MDA-modified proteins other than human MDA-modified lipoproteins exist in human sera [Kergonou, J. F., Bruna, B., Pennacino, I. & Ducousso, R., Advances in the Biosciences, 71, 121–124 (1988)]. Therefore, it is first necessary to take account of the possibility that the anti-human MDA-modified lipoprotein antibody may react with the other MDA-modified proteins. Accordingly, in the case where the denatured LDL is assayed, it is preferable to use a sandwich immunoassay making use of both antibodies which respectively recognize human MDA-modified LDL and human apoB constituting LDL so as to enhance the specificity for the detection of the human MDA-modified LDL. More specifically, one of an anti-human MDA-modified LDL monoclonal antibody and an anti-human apoB antibody is immobilized on an insoluble carrier, and the other is labeled with a labeling substance. These antibodies are then brought into contact with a vital sample to perform the sandwich immunoassay, thereby determining the human MDA-modified LDL.

In the case where the denatured Lp(a) is assayed, it is preferable to use a sandwich immunoassay making use of an antibody which recognizes human apo(a) constituting human MDA-modified Lp(a) so as to enhance the specificity for the detection of the human MDA-modified Lp(a). More specifically, one of an anti-human MDA-modified Lp(a) monoclonal antibody and an anti-human apo(a) antibody is immobilized on an insoluble carrier, and the other is labeled with a labeling substance. These antibodies are then brought into contact with a vital sample to perform the sandwich immunoassay, thereby determining the human MDA-modified Lp(a). Further, in the case where the denatured HDL is assayed, it is preferable to use a sandwich immunoassay making use of an antibody which recognize human apoA-I or apoA-II constituting human MDA-modified HDL so as to enhance the specificity for the detection of the human MDA-modified HDL. More specifically, one of an anti-human MDA-modified HDL monoclonal antibody and an anti-human apoA-I antibody or human apoA-II antibody is immobilized on an insoluble carrier, and the other is labeled with a labeling substance. These antibodies are then brought into contact with a vital sample to perform the sandwich immunoassay, thereby determining the human MDA-modified HDL.

Examples of the insoluble carrier used herein include various kinds of synthetic polymers such as polyethylene and polypropylene, glass, silicon, insoluble polysaccharides, and the like. These carriers may be used in the form of a sphere, a rod, fine particles or the like, or as a test tube, a microtiter plate or the like. The preparation of the insolubilized antibody is conducted by binding an antibody to an insoluble carrier by physical adsorption or covalent binding.

Examples of the labeling substance used in the labeled antibody include radioisotopes, enzymes, various kinds of fluorescent materials and fine particles such as colloidal gold. For example, in the case where an enzyme is used as a labeling substance for the labeled antibody, the enzyme-labeled antibody can be prepared by any known method. As necessary, an antibody to be used may be partially degested into $F(ab')_2$ by a suitable protease or further into Fab' in the presence of a reducing agent, and such a fragment may be then labeled with an enzyme. Examples of the enzyme used in labeling the antibody include β-D-galactosidase, peroxydase, alkaline phosphatase, glucose oxidase and the like.

The immune reaction may be either a one-step reaction or a two-step reaction. If the reaction is conducted by the one-step reaction, the surfactant may be added during the immune reaction. If the immune reaction is performed by two steps, the vital sample is first brought into contact with the insolubilized antibody in the first reaction to bind an antigen into an insolubilized antibody-antigen complex. In the second reaction, the enzyme-labeled antibody is then bound to this complex into an insolubilized antibody-antigen-enzyme-labeled antibody complex. In this two-step reaction, an buffer solution with which the surfactant has been caused to coexist is used in a liquid reaction mixture in the stage that the anti-denatured lipoprotein antibody is brought into contact with the antigen. More specifically, when the anti-denatured lipoprotein antibody is used as the insolubilized antibody or the labeled antibody, the buffer solution containing the surfactant therein is caused to coexist with the insolubilized antibody in the first reaction or the labeled antibody in the second reaction to conduct the immune reaction.

As the buffer solution, may be used those having a pH ranging from 6 to 10. As a buffer, glycine, tris, phosphate, imidazole, triethanolamine, barbiturate or Good's buffer may preferably be used in a range of 10–100 mM. In particular, it is preferable to use a buffer of glycine, HEPES (a kind of Good's buffer) or phosphate in a concentration of 10–50 mM so as to keep pH 7–9.

In order to stabilize the antigen and the antibodies in the liquid reaction mixture, it is further desirable that a suitable protein be caused to coexist with them. Examples of the protein include BSA, HSA, gelatin and the like. The protein may preferably be used in a concentration ranging from 0.05 to 2.0% (w/v). It is particularly preferable to use BSA in a range of 0.1–1.0% (w/v).

As necessary, a salt such as NaCl or KCl may be added in a concentration ranging from 10 to 300 mM for controlling ionic strength, and besides an antiseptic such as chlorhexidine or $NaN_3$ may be added for preventing the growth of bacteria.

In the case where the immune reaction is performed in two steps, no particular limitation is imposed on the kind of a buffer used in a step that the other anti-apoB antibody, anti-apo(a) antibody, anti-apoA-I antibody or anti-apoA-II antibody is reacted with the antigen, even when such an antibody is used in either the insolubilized antibody or the labeled antibody so far as the buffer can keep the immune reaction a suitable pH of 6–9.

The label activity of the complex thus obtained is then measured, whereby the amount of the denatured lipoprotein in the vital sample can be determined.

The present invention will hereinafter be described more specifically by reference to the following examples.

Incidentally, an anti-human MDA-modified LDL monoclonal antibody No. 29225 to be used in the following examples was produced in accordance with the procedure described in Example 1 of Japanese Patent Application Laid-Open No. 173096/1992.

EXAMPLE 1

Effect of SDS on Assaying System of MDA-modified LDL

The anti-human MDA-modified LDL monoclonal antibody No. 29225 was first prepared with a phosphate buffer solution (pH: 7.2)-saline (hereinafter referred to as "PBS") so as to give a concentration of 16 μg/ml. The thus-obtained preparation was then poured in portions of 100 μl/well into microplates. Each of the microplates was left at rest overnight at 4° C. to immobilize the antibody. After the microplate was then fully washed with distilled water, the antibody was blocked overnight at 4° C. in PBS containing 4% of non-fat dry milk. The antibody-bound plates thus obtained were used in reaction.

The following assaying procedure was followed to conduct the reaction. Namely, 25 mM of glycine buffer solution (pH: 9.0), which contained 0.2% of bovine serum albumin (BSA), 75 mM of NaCl and 0.1% of $NaN_3$, and were added separately with SDS in concentrations of 0, 0.75, 2.25, 3.75 and 5.25 mM (hereinafter called "SDS-containing BSA-Gly"), were separately added in portions of 100 μl/well to the antibody-bound plates. Dilute samples of a serum of person of health, which had been obtained by diluting the serum from 1/200 to 1/3200 in five steps with BSA-Gly, were separately poured in portions of 50 μl/well into the antibody-bound plates to start reaction. After reacted for 1 hour at 37° C., the plates were fully washed. A β-galactosidase-labeled anti-human apoB monoclonal antibody solution was then poured in portions of 100 μm/well into the antibody-bound plates to conduct reaction for 1 hour at 37° C. After fully washing the plates, O-nitrophenyl-β-D-galactopyranoside was used as a substrate to perform an enzyme reaction at 37° C. After 1 hour, a 0.1 M $Na_2CO_3$ solution was added in portions of 100 μm/well to the plates to stop the reaction. Thereafter, the absorbances of the liquid reaction mixtures in the individual plates were measured at a wavelength of 414 nm.

The results are as illustrated in FIG. 1, and revealed that in the reaction system to which no SDS is added, the MDA-modified LDL in the serum cannot be detected at all, while the MDA-modified LDL in the serum can be determined by adding SDS to the reaction system.

EXAMPLE 2

Identification of Specificity of Assaying System of MDA-modified LDL Making use of MDA-modified Human Serum Albumin (HSA)

The preparation of MDA modified HSA was conducted in accordance with the method described in Example 1 of Japanese Patent Application Laid-Open No. 173096/1992. More specifically, HSA and MDA were dissolved in 50 mM of a phosphate buffer solution (pH: 6) so as to give final concentrations of 3 mg/ml and 16.7 mM, respectively, to react them at 25° C. for 5 hours. The liquid reaction mixture was cooled to 4° C. to stop the reaction, and then dialyzed at 4° C. to PBS containing 100 μM of EDTA. The thus-obtained product was used as MDA-modified HSA.

Antibody-bound plates prepared in the same manner as in Example 1 were used in reaction.

Samples used in the reaction were prepared by mixing, in a proportion of 1:1, a dilute serum of person of health which had been obtained by diluting the serum to 1/3200 with 25 mM of a phosphate buffer solution (pH: 7.2) containing 0.5% of BSA, 150 mM of NaCl and 0.05% of $NaN_3$ in advance (hereinafter called "BSA-PBS") with individual BSA-PBSs that the concentrations of MDA-modified HSA or HSA contained therein were 0, 1, 10 and 100 μg/ml.

The following assaying procedure was followed. Namely, BSA-PBS containing 2.5 mM of SDS was added in portions of 100 μl/well to the antibody-bound plates. Thereafter, the samples prepared in the above-described manner were separately poured in portions of 50 μl/well into the plates to start reaction. Thereafter, the procedure of Example 1 was followed to conduct the succeeding steps of the assay.

This example is intended to use the nature of the MDA-modified HSA that reacts with the anti-MDA-modified LDL monoclonal antibody coated on the plate, so as to demonstrate that if the substance detected in the assay of the present invention is MDA-modified LDL in the blood, the MDA-modified LDL undergoes competitive inhibition against the MDA-modified HSA added to the reaction system.

Figure 2:
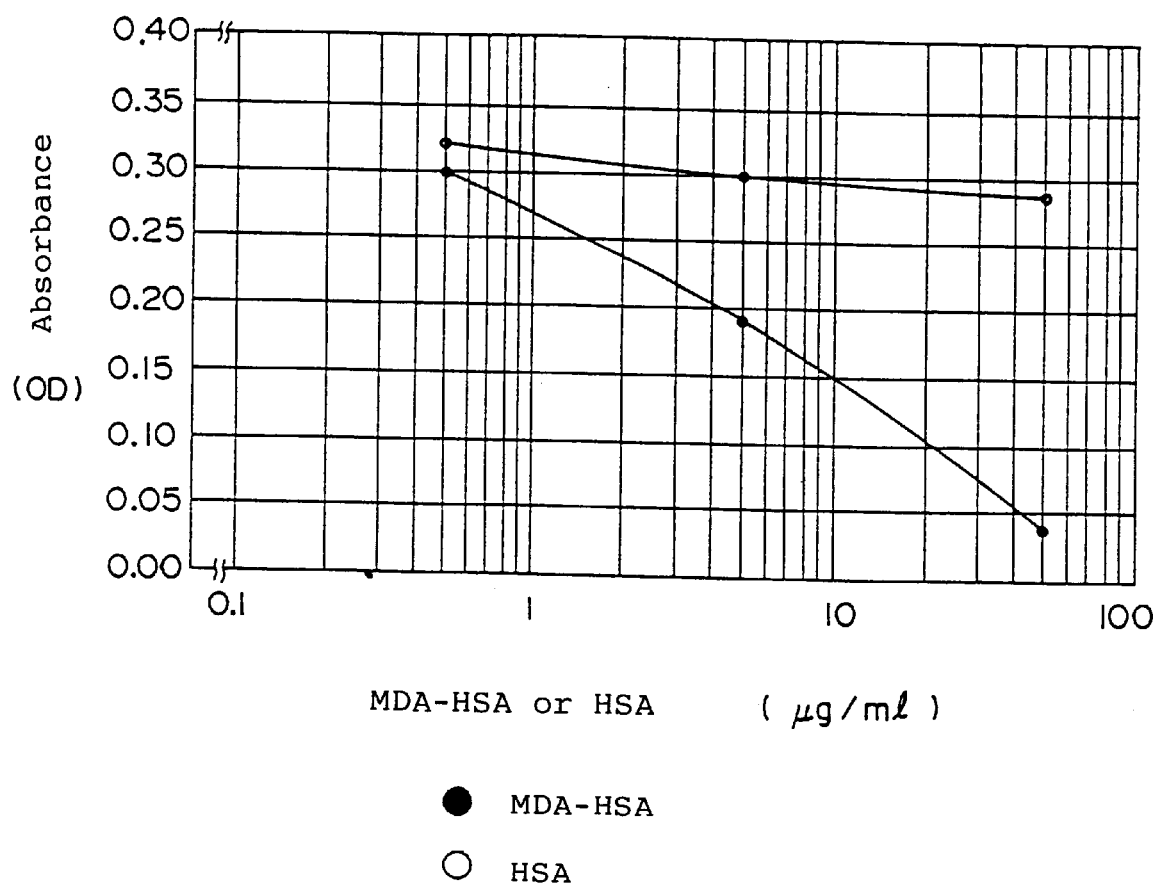
FIG. 2 diagrammatically illustrates the relationship between the concentration of MDA-modified HSA or HSA and inhibitory effect upon the reaction of an anti-human MDA-modified LDL monoclonal antibody with a mixture of a human serum and MDA-modified HSA or HSA in the presence of SDS.

The results are as illustrated in FIG. 2 and revealed that the addition of HSA does not affect the reaction, but the addition of MDA-modified HSA inhibits the reaction in proportion to the concentration thereof. This indicates that the assay of the present invention can specifically detect the MDA-modified LDL in the blood.

EXAMPLE 3

Reactivity of Assaying System to Lipoprotein Fractions

Lipoprotein fractions were first obtained from a fresh human serum by an ultracentrifugation known per se in the art. More specifically, after chylomicron was removed from the fresh human serum by centrifugation, KBr was added to adjust the specific density d of the serum. The thus-adjusted serum was fractionated by step-wise ultracentrifugation into fractions respectively having specific densities of d<1.019, 1.019<d<1.063, and 1.063<d<1.21, which were regarded as "very low density lipoprotein (VLDL)+intermediate density lipoprotein (IDL)", "LDL" and "high density lipoprotein (HDL)", respectively. The individual lipoprotein fractions were dialyzed to PBS containing 100 $\mu$M of EDTA and then subjected to determination of protein by the Lowry method. A part of LDL was bound with MDA (MDA-modified LDL was prepared in the same manner as the MDA modification of HSA in Example 2), and the MDA-modified LDL thus obtained was then dialyzed to PBS containing 100 $\mu$M of EDTA like the individual lipoprotein fractions and moreover subjected to determination of protein by the Lowry method.

Portions of the thus-prepared lipoproteins were respectively diluted with BSA-Gly (see Example 1) so as to give concentrations of 0.01, 0.04, 0.2 and 1.0 $\mu$g/ml for the MDA-modified LDL, and of 0.5, 5.0, 50 and 500 $\mu$g/ml for the other lipoprotein fractions, thereby preparing samples.

The following assaying procedure was followed. Namely, BSA-Gly containing 3.75 mM of SDS was added in portions of 100 $\mu$l/well to antibody-bound plates prepared in the same manner as in Example 1, and the samples prepared above were separately poured in portions of 50 $\mu$l/well into the plates to start reaction. Thereafter, the procedure of Example 1 was followed to conduct the succeeding steps of the assay.

Figure 3:
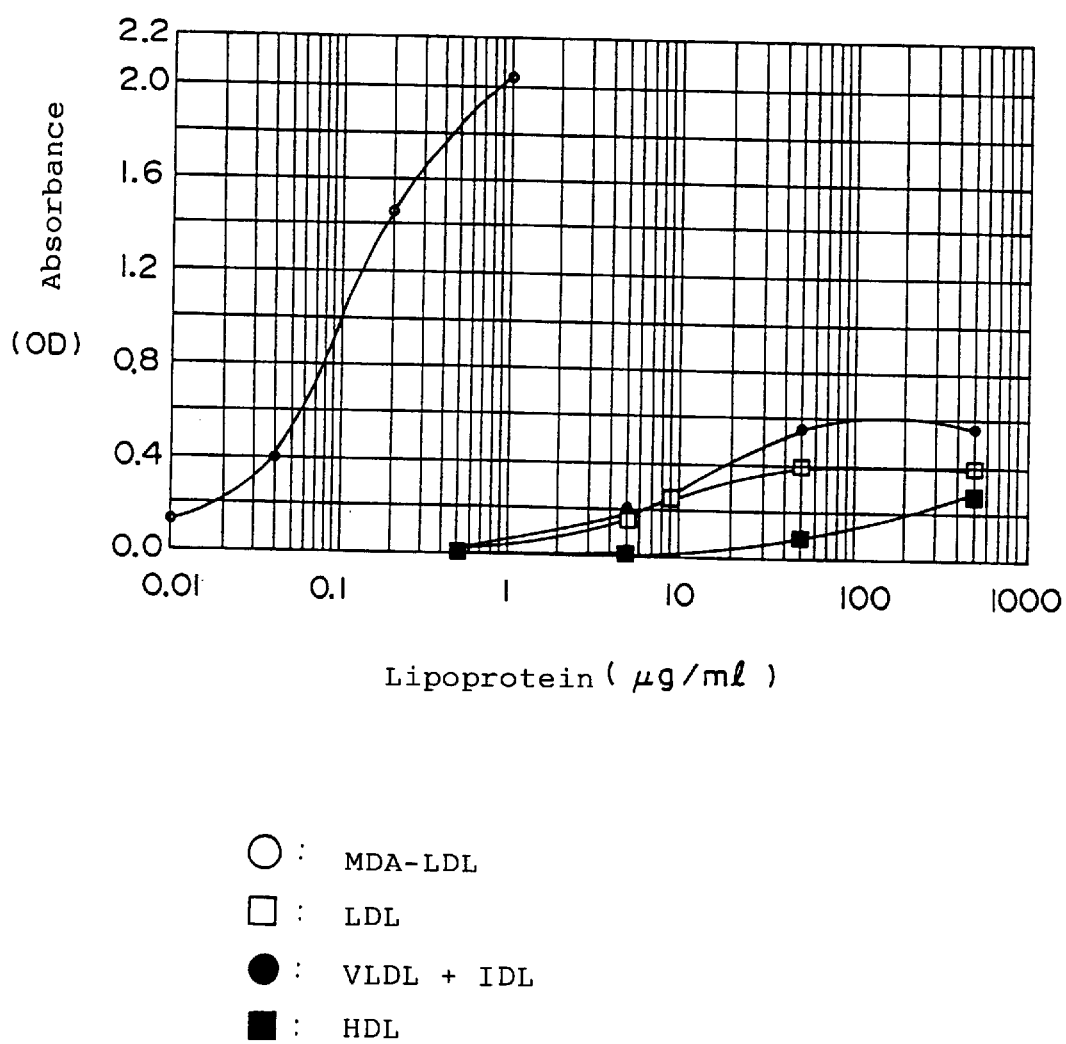
FIG. 3 diagrammatically illustrates reactivities of an anti-human MDA-modified LDL monoclonal antibody to MDA-modified LDL, LDL, VLDL (very low density lipoprotein), IDL (intermediate density lipoprotein) and HDL, respectively.

The results are as illustrated in FIG. 3 and revealed that even LDL and VLDL+IDL, which are lipoproteins containing apoB, show only reactivity as low as about 1/1000 compared with that of the MDA-modified LDL.

EXAMPLE 4

Assay of MDA-modified LDL Added with Sodium Dodecylbenzenesulfonate as Anionic Surfactant Antibody-bound plates prepared in the same manner as in Example 1 were used in reaction.

The following assaying procedure was followed. Namely, PBS (see Example 1) containing 0.1% of BSA, to which 8.6 mM of sodium dodecylbenzenesulfonate had been added, was added in portions of 100 $\mu$l/well to the antibody-bound plates. Further, dilute samples of a human serum, which had been obtained by diluting the serum from 1/400 to 1/3200 in four steps with PBS containing 0.1% of BSA, were separately poured in portions of 50 $\mu$l/well into the antibody-bound plates to start reaction. Thereafter, the procedure of Example 1 was followed to conduct the succeeding steps of the assay.

Figure 4:
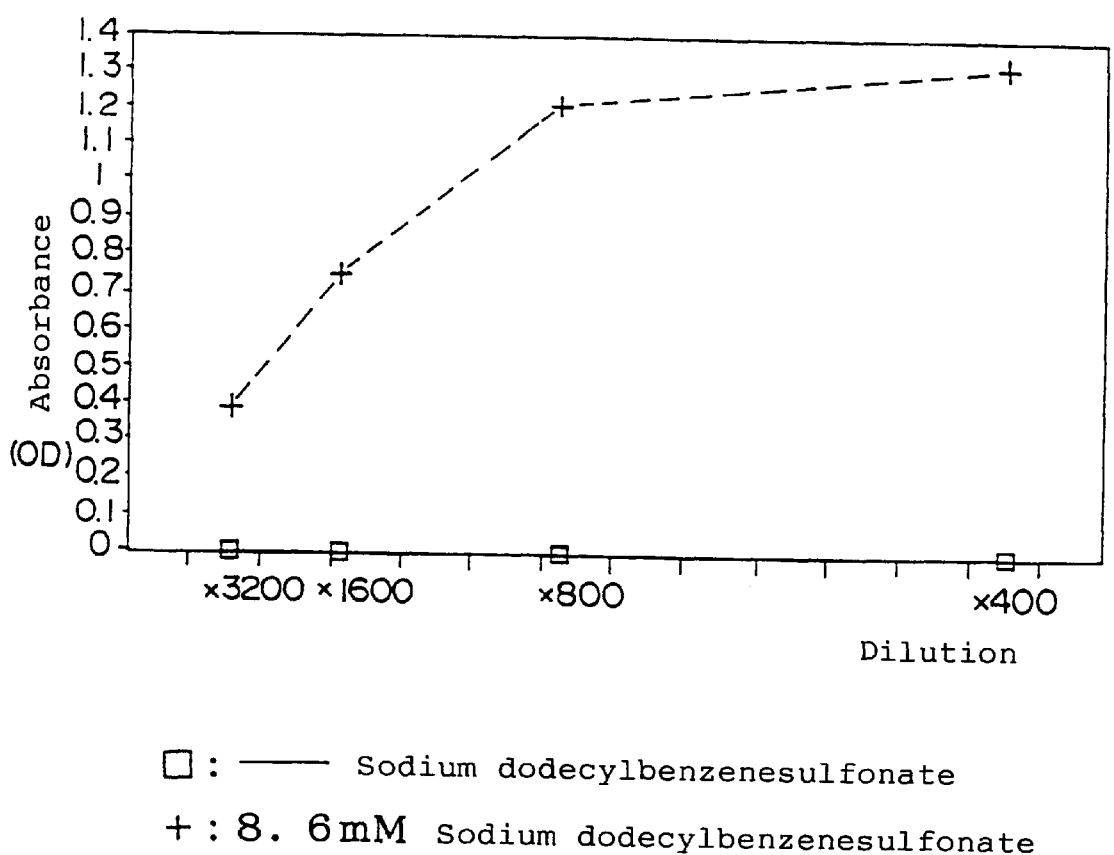
FIG. 4 diagrammatically illustrates the relationship between the dilution of a human serum and enzymatic activity upon assaying MDA-modified LDL in a human serum in the absence or presence of sodium dodecylbenzenesulfonate using an anti-human MDA-modified LDL monoclonal antibody.

The results are as illustrated in FIG. 4, and revealed that in the reaction system to which no sodium dodecylbenzenesulfonate is added, the MDA-modified LDL in the serum cannot be detected at all, while the MDA-modified LDL in the serum can be determined by adding sodium dodecylbenzenesulfonate to the reaction system.

EXAMPLE 5

Sera of 49 persons of health, 31 diabetics and 21 cases of an arteriosclerotic disease were used as specimens to determine the amount of MDA-modified LDL contained in each serum according to the method of Example 1.

Namely, antibody-bound plates prepared in the same manner as in Example 1 were used in reaction, and the following assaying procedure was followed. Each of the sera diluted to 1/401 and BSA-Gly containing 3.75 mM of SDS were added in proportions of 50 $\mu$l/well and 100 $\mu$l/well, respectively, to the antibody-bound plate. Thereafter, the procedure of Example 1 was followed to conduct the succeeding steps of the assay.

Figure 5:
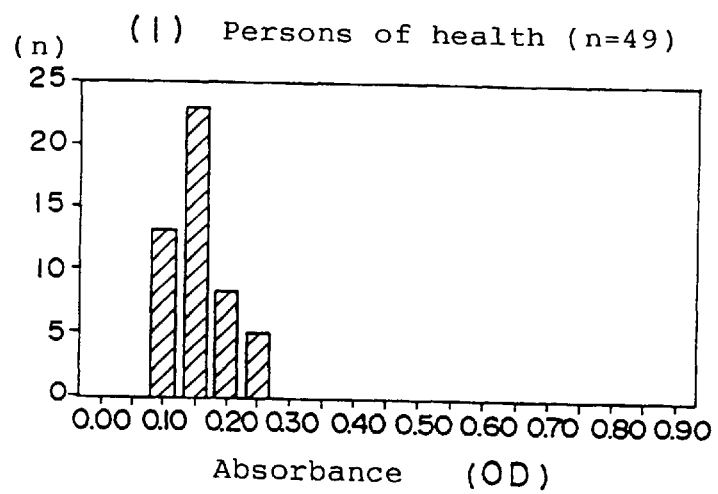
FIG. 5 diagrammatically illustrates the relationship between individual sera and enzymatic activity upon assaying MDA-modified LDL in sera of persons of health, diabetics and cases of an arteriosclerotic disease according to the method of the present invention.
Figure 5:
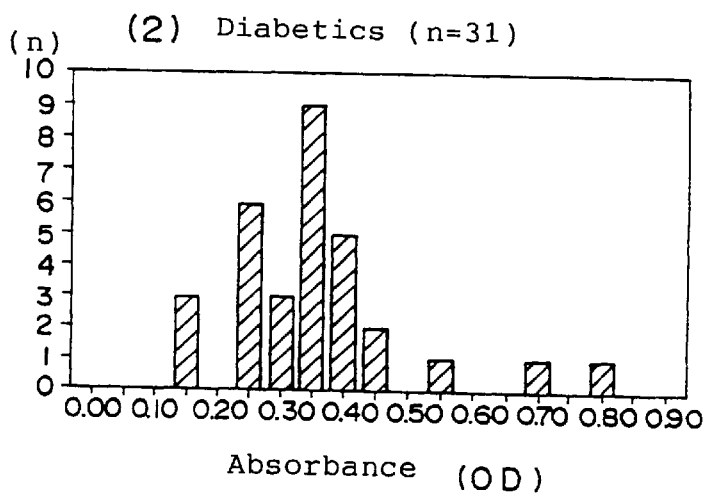
Figure 5:
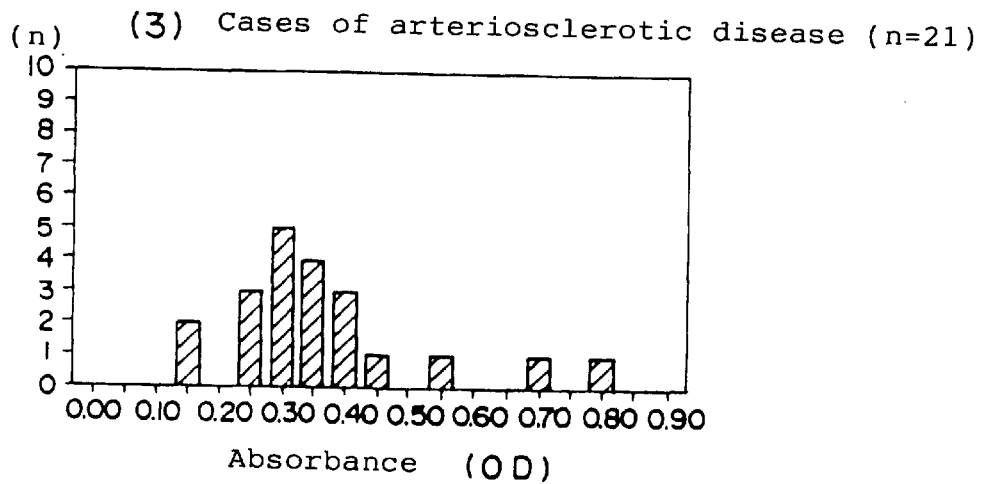

The results are as illustrated in FIGS. 5(1)–5(3), and revealed that the MDA-modified LDL exists in plenty in the sera of the cases of diabetes and arteriosclerotic disease compared with the sera of the persons of health.

EXAMPLE 6

Effect of SDS on Assaying System of MDA-modified Lp(a)

An anti-human MDA-modified Lp(a) monoclonal antibody No. 29225 (corresponding to the anti-human MDA-modified LDL monoclonal antibody described in Japanese Patent Application Laid-Open No. 173096/1992) was first prepared with PBS so as to give a concentration of 16 $\mu$g/ml. The thus-obtained preparation was then poured in portions of 100 $\mu$l/well into microplates. Each of the microplates was left at rest overnight at 4° C. to immobilize the antibody. After the microplate was then fully washed with PBS containing 0.05% of Tween 20 (hereinafter referred to as "PBST"), the antibody was blocked overnight at 4° C. in PBS containing 4% of non-fat dry milk. The antibody-bound plates thus obtained were used in reaction.

The following assaying procedure was followed to conduct the reaction. Namely, 25 mM of HEPES buffer solution (pH: 7.0), which contained 0.2% of BSA, 30 mM of NaCl and 0.1% of NaN$_3$ (hereinafter called "BSA-HEPES"), and were added separately with SDS in concentrations of 0, 3.75, 6.75, 9.75 and 15.75 mM, were separately added in portions of 100 $\mu$l/well to the antibody-bound plates. Dilute samples of a human serum, which had been obtained by diluting the serum from 1/50 to 1/400 in four steps with BSA-HEPES, were separately poured in portions of 50 $\mu$l/well into the antibody-bound plates to start reaction. After reacted for 1 hour at room temperature, the plates were fully washed. A $\beta$galactosidase-labeled anti-human apo(a) monoclonal antibody solution was then poured in portions of 100 $\mu$m/well into the antibody-bound plates to conduct reaction for 1 hour at room temperature. After fully washing the plates, O-nitrophenyl-$\beta$-D-galactopyranoside was used as a substrate to perform an enzyme reaction at room temperature. After 1 hour, a 0.1 M Na$_2$CO$_3$ solution was added in portions of 100 $\mu$m/well to the plates to stop the reaction. Thereafter, the absorbances of the liquid reaction mixtures in the individual plates w ere measured at a wavelength of 414 nm (reference wavelength: 690 nm).

Figure 6:
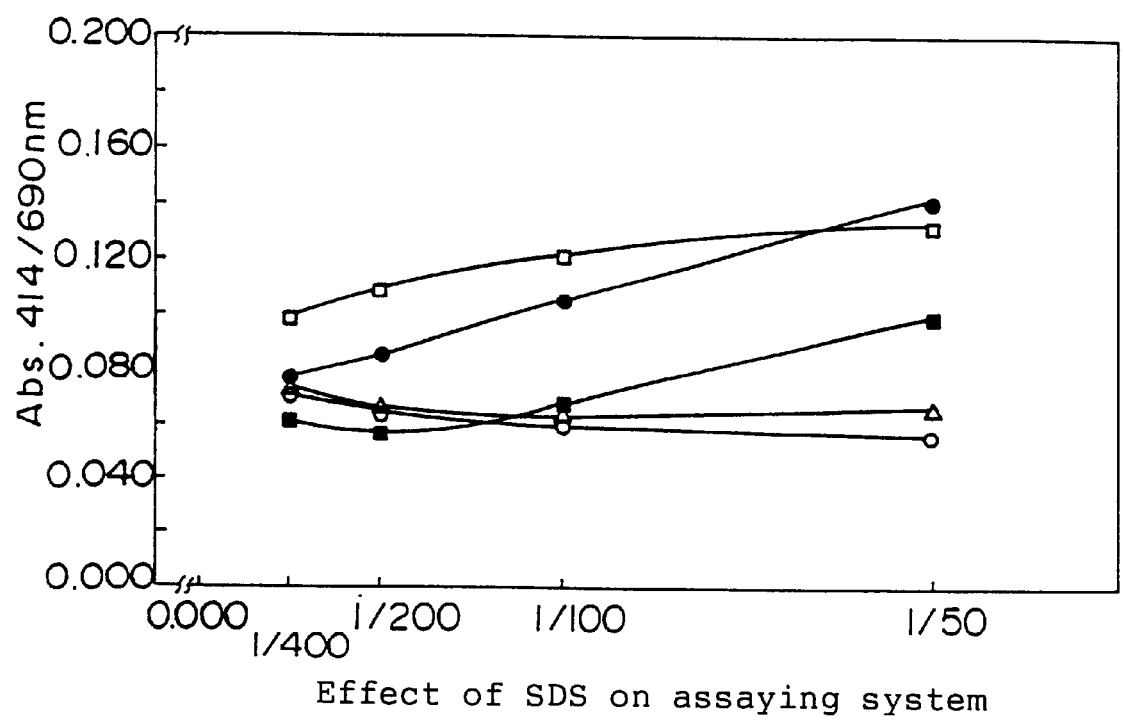
FIG. 6 diagrammatically illustrates the effect of SDS on an assaying system for MDA-modified Lp(a) in a human serum using an anti-MDA-bound Lp(a) monoclonal antibody.

The results are as illustrated in FIG. 6, and revealed that in the reaction system to which no SDS is added, the MDA-modified Lp(a) in the serum cannot be detected at all, while the MDA-modified Lp(a) in the serum can be determined by adding SDS to the reaction system.

EXAMPLE 7

Identification of Specificity of Assaying System of MDA-modified Lp(a) Making use of MDA-bound Human Serum Albumin (HSA)

The preparation of MDA modified HSA was first conducted. HSA and MDA were dissolved in 50 mM of an acetate buffer solution (pH: 4) so as to give final concentrations of 9 mg/ml and 133.3 mM, respectively, to react them at 25° C. for 5 hours. The liquid reaction mixture was cooled at 4° C. to stop the reaction, and then dialyzed at 4° C. to a 25 mM HEPES buffer solution (pH: 7) containing 30 mM of NaCl and 0.1% of NaN$_3$. The thus-obtained product was used as MDA-modified HSA. Besides, antibody-bound plates prepared in the same manner as in Example 6 were used in reaction. Samples used in the reaction were prepared by mixing, in a proportion of 1:1, a dilute human serum which had been obtained by diluting the serum to 1/50 with BSA-HEPES (see Example 6) with individual BSA-HEPESs that the concentrations of MDA-bound HSA or HSA contained therein were 0, 10, 100 and 500 μg/ml.

The following assaying procedure was followed. Namely, BSA-HEPES containing 6.75 mM of SDS was added in portions of 100 μl/well to the antibody-bound plates. Thereafter, the samples prepared in the above-described manner were separately poured in portions of 50 μl/well into the plates to start reaction. After reacted for 1.5 hours at room temperature, the plates were fully washed. A β-galactosidase-labeled anti-human apo(a) monoclonal antibody solution was the n p our ed in portions of 100 μm/well into the antibody-bound plates to conduct reaction for 1.5 hours at room temperature. After fully washing the plates, O-nitrophenyl-β-D-galactopyranoside was used as a substrate to perform an enzyme reaction at room temperature. After 1.5 hours, a 0.1 M $Na_2CO_3$ solution was added in portions of 100 μl/well to the plates to stop the reaction. Thereafter, the absorbances of the liquid reaction mixtures in the individual plates were measured at a wavelength of 414 nm (reference wavelength: 690 nm).

This example is intended to use the nature of the MDA-modified HSA that reacts with the anti-MDA-modified Lp(a) monoc lonal an tibody coated on the plate, so as to demonstrate that if the substance detected in the assay of the present invention is MDA-modified Lp(a) in the blood, the MDA-miodified Lp(a) undergoes competitive inhibition against the MDA-modified HSA added to the reaction system.

Figure 7:
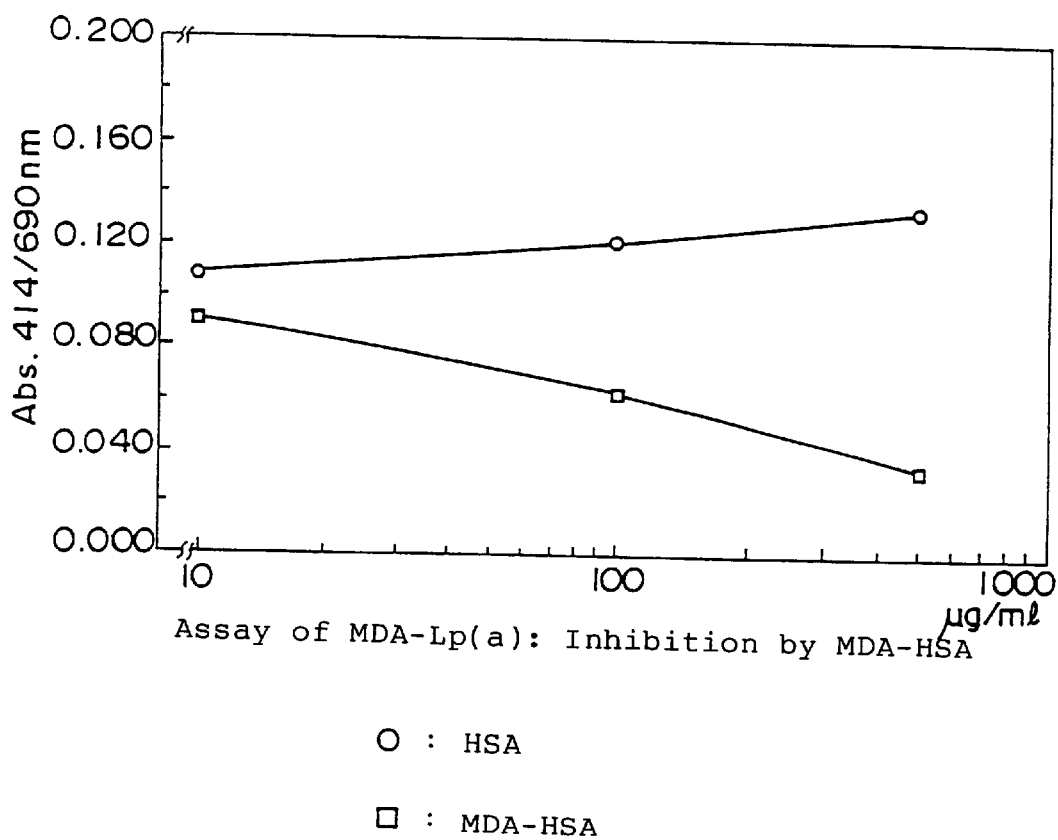
FIG. 7 diagrammatically illustrates the relationship between the concentration of MDA-modified HSA or HSA and inhibitory effect upon the reaction of an anti-MDA-modified Lp(a) monoclonal antibody with a mixture of a human serum and MDA-modified HSA or HSA in the presence of SDS.

The results are as illustrated in FIG. 7 and revealed that the addition of HSA does not affect the reaction, but the addition of MDA-modified HSA inhibits the reaction in proportion to the concentration thereof. This indicates that the assay of the present invention can specifically detect the MDA-modified Lp(a) in the blood.

EXAMPLE 8

Assay of MDA-modified Lp(a) Added with Sodium Dodecylbenzenesulfonate as Anionic Surfactant Antibody-bound plates prepared in the same manner as in Example 6 were used in reaction.

The following assaying procedure was followed. Namely, solutions of BSA-HEPES (see Example 6), to which sodium dodecylbenzenesulfonate had been added in concentrations of 0, 1, 5 and 10 mM, respectively, were added in portions of 100 μl/well to the antibody-bound plates. Further, dilute samples of a human serum, which had been obtained by diluting the serum from 1/50 to 1/400 in four steps with BSA-HEPES, were separately poured in portions of 50 μl/well into the antibody-bound plates to start reaction. Thereafter, the procedure of Example 7 was followed to conduct the succeeding steps of the assay.

Figure 8:
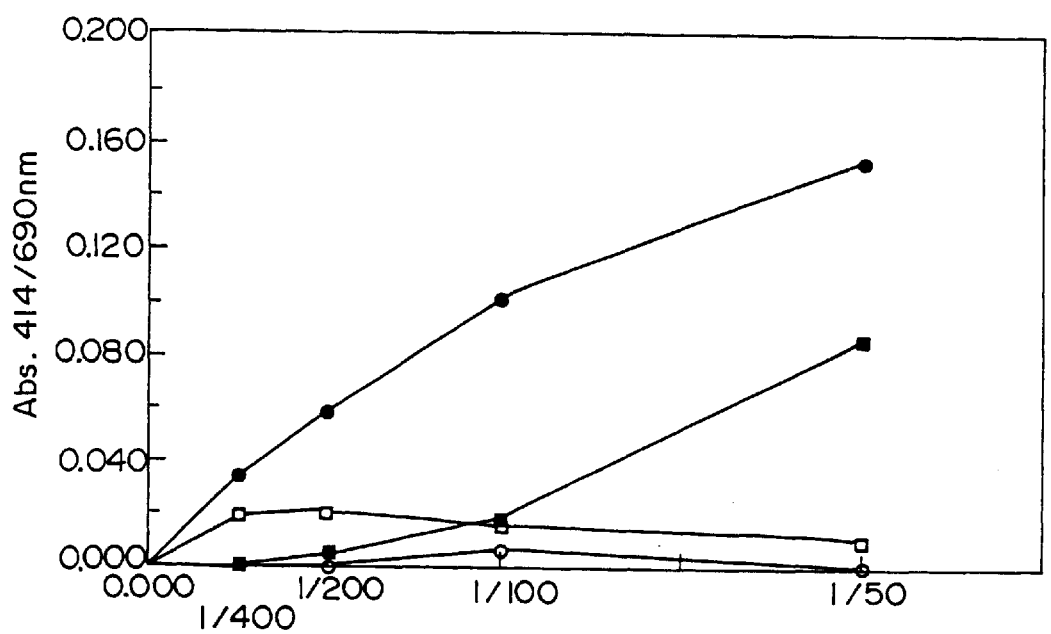
FIG. 8 diagrammatically illustrates the relationship between the dilution of a human serum and enzymatic activity upon assaying MDA-modified Lp(a) in a human serum in the absence or presence of sodium dodecylbenzenesulfonate using an anti-MDA-modified Lp(a) monoclonal antibody.

The results are as illustrated in FIG. 8, and revealed that in the reaction system to which no sodium dodecylbenzenesulfonate is added, the MDA-modified Lp(a) in the serum cannot be detected at all, while the MDA-modified Lp(a) in the serum can be determined by adding sodium dodecylbenzenesulfonate to the reaction system.

EXAMPLE 9

Assay of MDA-modified Lp(a) Added with Cetyltrimethylammonium Chloride as Cationic Surfactant Antibody-bound plates prepared in the same manner as in Example 6 were used in reaction.

The following assaying procedure was followed. Namely, solutions of BSA-HEPES (see Example 6), to which cetyltrimethylammonium chloride had been added in concentrations of 0, 5, 10 and 20 mM, respectively, were added in portions of 100 μl/well to the antibody-bound plates. Further, dilute samples of a human serum, which had been obtained by diluting the serum from 1/100 to 1/400 in three steps with BSA-HEPES, were separately poured in portions of 50 μl/well into the antibody-bound plates to start reaction. Thereafter, the procedure of Example 7 was followed to conduct the succeeding steps of the assay.

Figure 9:
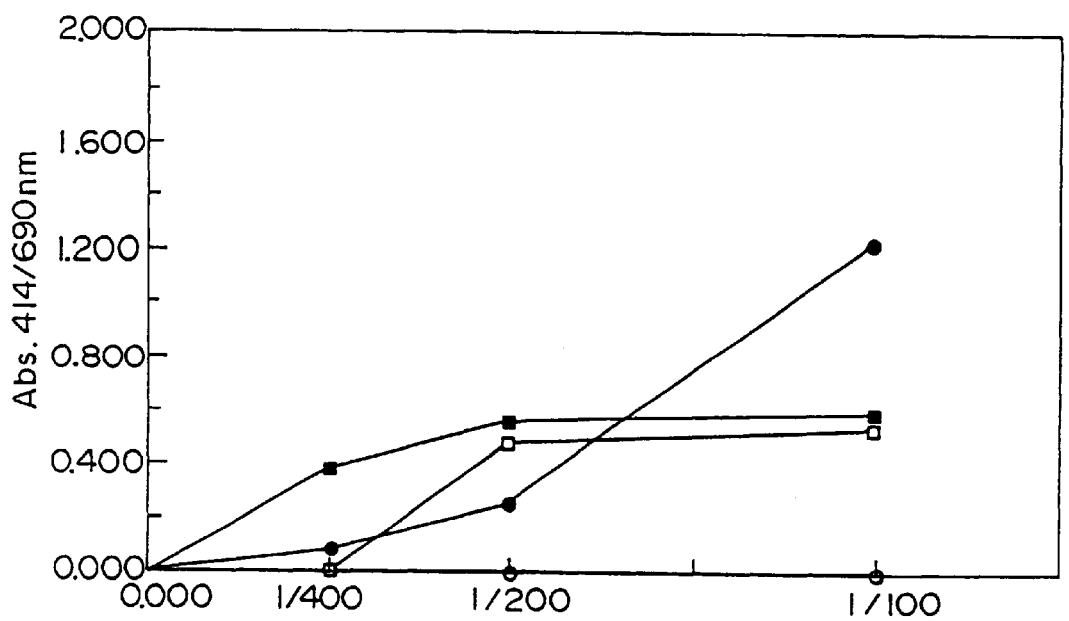
FIG. 9 diagrammatically illustrates the relationship between the dilution of a human serum and enzymatic activity upon assaying MDA-modified Lp(a) in a human serum in the absence or presence of cetyltrimethylammonium chloride using an anti-MDA-modified Lp(a) monoclonal antibody.

The results are as illustrated in FIG. 9, and revealed that in the reaction system to which no cetyltrimethylammonium chloride is added, the MDA-modified Lp(a) in the serum cannot be detected at all, while the MDA-modified Lp(a) in the serum can be determined by adding cetyltrimethylammonium chloride to the reaction system.

EXAMPLE 10

Assay of MDA-modified Lp(a) Added with Polyoxyethylene Secondary Alkyl Ether as Nonionic Surfactant Antibody-bound plates prepared in the same manner as in Example 6 were used in reaction.

The following assaying procedure was followed. Namely, solutions of BSA-HEPES (see Example 6), to which a polyoxyethylene secondary alkyl ether had been added in concentrations of 0, 0.05, 0.2 and 0.5%, respectively, were added in portions of 100 μl/well to the anti-bodybound plates. Further, dilute samples of a human serum, which had been obtained by diluting the serum from 1/300 to 1/2700 in three steps with BSA-HEPES, were separately poured in portions of 50 μl/well into the antibody-bound plates to start reaction. After reacted for 1.5 hours at room temperature, the plates were fully washed. A β-galactosidase-labeled anti-human apo(a) monoclonal antibody solution was then poured in portions of 100 μm/well into the antibody-bound plates to conduct reaction for 1.5 hours at room temperature. After fully washing the plates, O-nitrophenyl-β-D-galactopyranoside was used as a substrate to perform an enzyme reaction at room temperature. After 30 minutes, a 0.1 M $Na_2CO_3$ solution was added in portions of 100 μl/well to the plates to stop the reaction. Thereafter, the absorbances of the liquid reaction mixtures in the individual plates were measured at a wavelength of 414 nm (reference wavelength: 690 nm).

Figure 10:
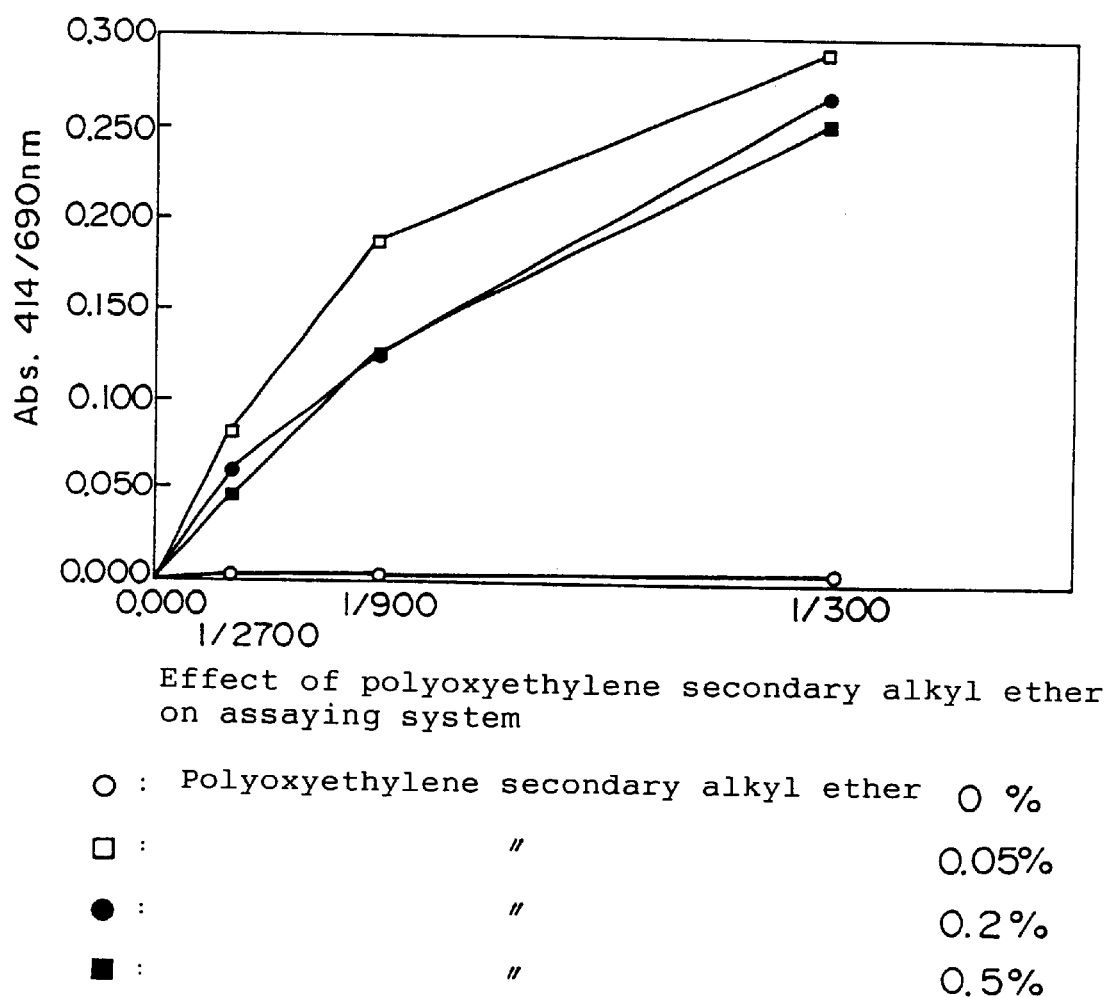
FIG. 10 diagrammatically illustrates the relationship between the dilution of a human serum and enzymatic activity upon assaying MDA-modified Lp(a) in a human serum in the absence or presence of a polyoxyethylene secondary alkyl ether using an anti-MDA-modified Lp(a) monoclonal antibody.

The results are as illustrated in FIG. 10, and revealed that in the reaction system to which no polyoxyethylene secondary alkyl ether is added, the MDA-modified Lp(a) in the serum cannot be detected at all, while the MDA-modified Lp(a) in the serum can be determined by adding the polyoxyethylene secondary alkyl ether to the reaction system.

EXAMPLE 11

Sera of 25 persons of health, 13 diabetics and 10 cases of an arteriosclerotic disease were used as specimens to determine the amount of MDA-modified Lp(a) contained in each serum according to the method of Example 7.

Namely, antibody-bound plates prepared in the same manner as in Example 6 were used in reaction, and the following assaying procedure was followed. Each of the sera diluted to 1/50 and BSA-HEPES containing 6.75 mM of SDS were added in proportions of 50 μl/well and 100 μl/well, respectively, to the antibody-bound plate. Thereafter, the procedure of Example 7 was followed to conduct the succeeding steps of the assay.

Figure 11:
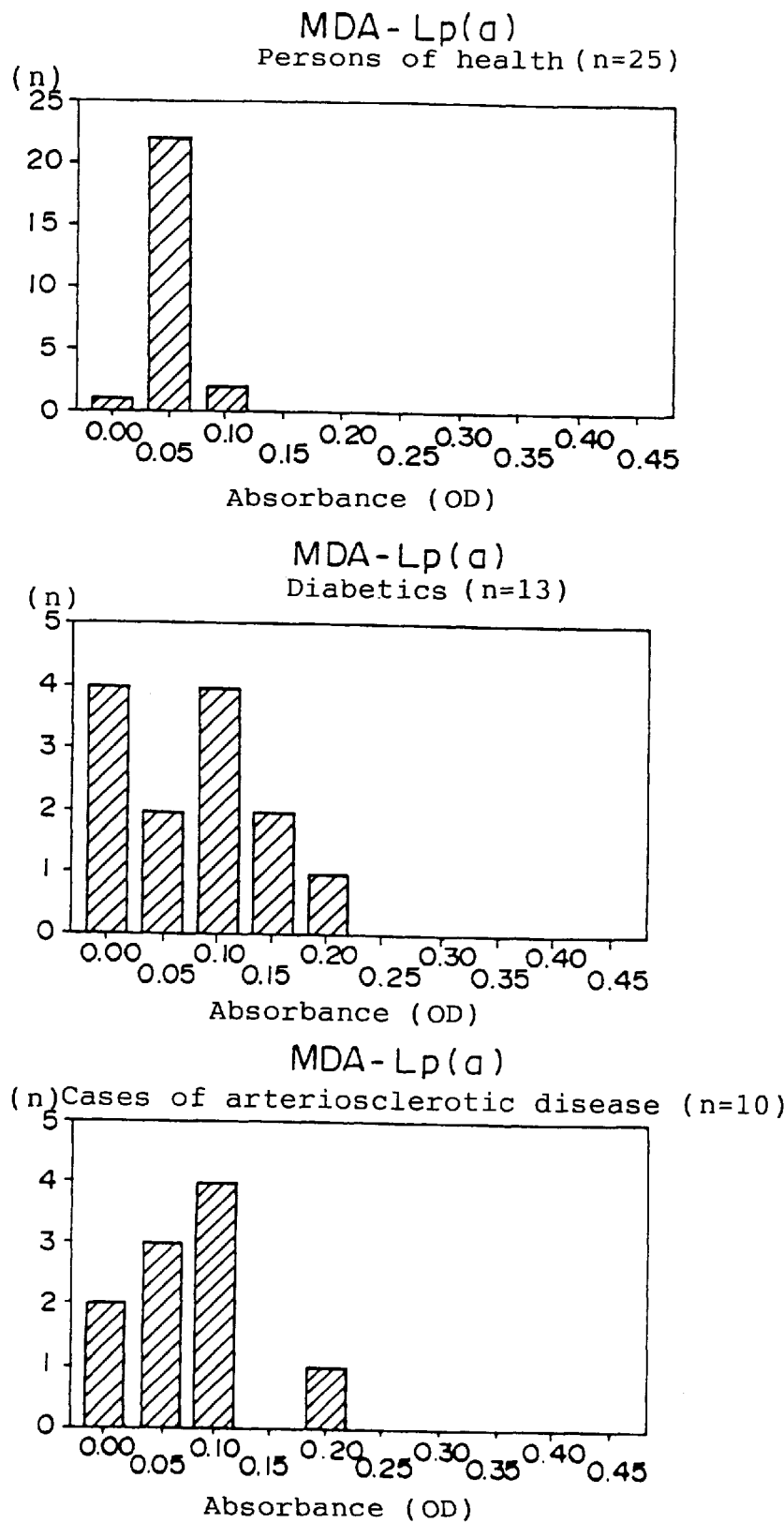
FIG. 11 diagrammatically illustrates the relationship between individual sera and enzymatic activity upon assaying MDA-modified Lp(a) in sera of persons of health, diabetics and cases of an arteriosclerotic disease according to the method of the present invention.

The results are as illustrated in FIGS. 11(1)–11(3), and revealed that the MDA-modified Lp(a) exists in plenty in the sera of the cases of diabetes and arteriosclerotic disease compared with the sera of the persons of health.

What is claimed is:

1. A solid phase sandwich assay procedure for assaying MDA modified lipoprotein in a body fluid sample which comprises immobilizing one of a pair of antibodies on an insoluble carrier to form an immobilized antibody on said carrier and labeling the other antibody of said pair with a labeling substance wherein one antibody of said pair recognizes human MDA modified lipoprotein and the other antibody of said pair recognizes an apolipoprotein component of said lipoprotein;

adding surfactant to said body fluid sample to form a mixture of body fluid sample and surfactant whereby said surfactant exposes an unexposed modified site on any MDA modified lipoprotein contained in said mixture;

contacting said pair of antibodies with said mixture whereby an immune reaction occurs; and detecting the presence of MDA modified lipoprotein bound to said insoluble carrier.

2. The method of claim 1 wherein the surfactant which is added to said body fluid sample is a buffered surfactant solution.

3. The method of claim 1 wherein the surfactant is an anionic surfactant.

4. The procedure of claim 1 wherein the antibodies of said pair are monoclonal antibodies.

5. The method of claim 4 wherein said pair of antibodies is selected from the group of pairs consisting of:
1) Antibody which recognizes human MDA modified LDL and antibody which recognizes human apoB component of said LDL,
2) Antibody which recognizes human MDA modified Lp(a) and antibody which recognizes human apo(a) component of said Lp(a), and
3) Antibody which recognizes human MDA modified HDL and antibody which recognizes human apoA-I or apoA-II component of said HDL.

6. The method of claim 5 in which said surfactant is added to said body fluid sample during said immune reaction.

7. The method of claim 5 wherein the labelling substance is an enzyme.

8. The method of claim 5 wherein stabilizing protein is included in said body fluid sample to stabilize the antigens and antibodies contained therein.

9. The method of claim 5 in which the immune reaction is performed in a first reaction wherein said body fluid sample is first brought into contact with said antibody previously immobilized on said carrier whereby said first reaction takes place in which antigen to said immobilized antibody becomes immobilized on to said carrier to form an immobilized antibody-antigen complex and then, in a second reaction, the labeled antibody is bound to said antibody-antigen complex to form an immobilized antibody-antigen-labeled antibody complex; and said surfactant is added in the form of a buffered solution to said body fluid sample during the step in which the antibody to said MDA modified lipoprotein is contacted with said MDA modified lipoprotein.

10. The method of claim 9 wherein the immobilized antibody is the antibody which recognizes said MDA modified lipoprotein and said buffered surfactant solution is added during said first reaction.

11. The method of claim 9 wherein the labeled antibody is the antibody which recognizes said MDA modified lipoprotein and said buffered surfactant solution is added during said second reaction.

12. The method of claim 9 wherein the surfactant is an anionic surfactant.

13. A method for detecting, in a body fluid sample, the presence of MDA modified lipoprotein having an unexposed modified site, which comprises:

obtaining a body fluid sample suspected of containing said MDA modified lipoprotein having an unexposed modified site;

adding surfactant to said body fluid sample to form a mixture of said body fluid sample and surfactant whereby said surfactant exposes said unexposed modified site to thereby produce a MDA modified lipoprotein having an exposed modified site in said mixture;

reacting said MDA modified lipoprotein having said exposed modified site with an antibody which is capable of specifically binding with said MDA modified lipoprotein having an exposed modified site to form a detectable antibody-modified lipoprotein complex, said reaction being accomplished by contacting said antibody with said mixture of body fluid sample and surfactant; and then detecting the presence of said detectable antibody-modified lipoprotein complex.

14. The method according to claim 13, wherein the MDA modified lipoprotein is selected from the group consisting of MDA modified low density lipoprotein, MDA modified lipoprotein (a) and MDA modified high density lipoprotein.

15. The method according to claim 13, wherein the antibody which recognized the MDA modified lipoprotein is an anti-malondialdehyde-modified lipoprotein antibody.

16. The method of claim 13 wherein said denatured lipoprotein is contacted with said surfactant by adding a buffered surfactant solution to said sample.

17. The method of claim 16 wherein the surfactant is an anionic surfactant.

18. The method of claim 13 which further includes the step of measuring antibody-MDA modified lipoprotein complex.

19. The method according to claim 18, wherein the antibody which is capable of specificallybinding with said MDA modified lipoprotein having an exposed modified site is an anti-malondialdehyde-modified lipoprotein antibody.

20. The method according to claim 19, wherein the MDA modified lipoprotein is selected from the group consisting of MDA modified low density lipoprotein, MDA modified lipoprotein (a) and MDA modified high density lipoprotein.

21. The method of claim 18 wherein the antibody which is capable of specifically binding with said MDA modified lipoprotein having an exposed modified site is a monoclonal antibody.

22. The method according to claim 21, wherein the MDA modified lipoprotein is selected from the group consisting of MDA modified low density lipoprotein, MDA modified lipoprotein (a) and MDA modified high density lipoprotein.

23. The method according to claim 21, wherein the surfactant is an anionic surfactant.

24. The method according to claim 23, wherein the MDA modified lipoprotein is selected from the group consisting of MDA modified low density lipoprotein, MDA modified lipoprotein (a) and MDA modified high density lipoprotein.

25. The method according to claim 23, wherein the anionic surfactant is an alkylsulfate.

26. The method according to claim 25, wherein the MDA modified lipoprotein is selected from the group consisting of MDA modified low density lipoprotein, MDA modified lipoprotein (a) and MDA modified high density lipoprotein.

* * * * *